Sept. 18, 1973 C. G. KLEHM Plant Pat. 3,395
PEONY PLANT
Filed March 9, 1972
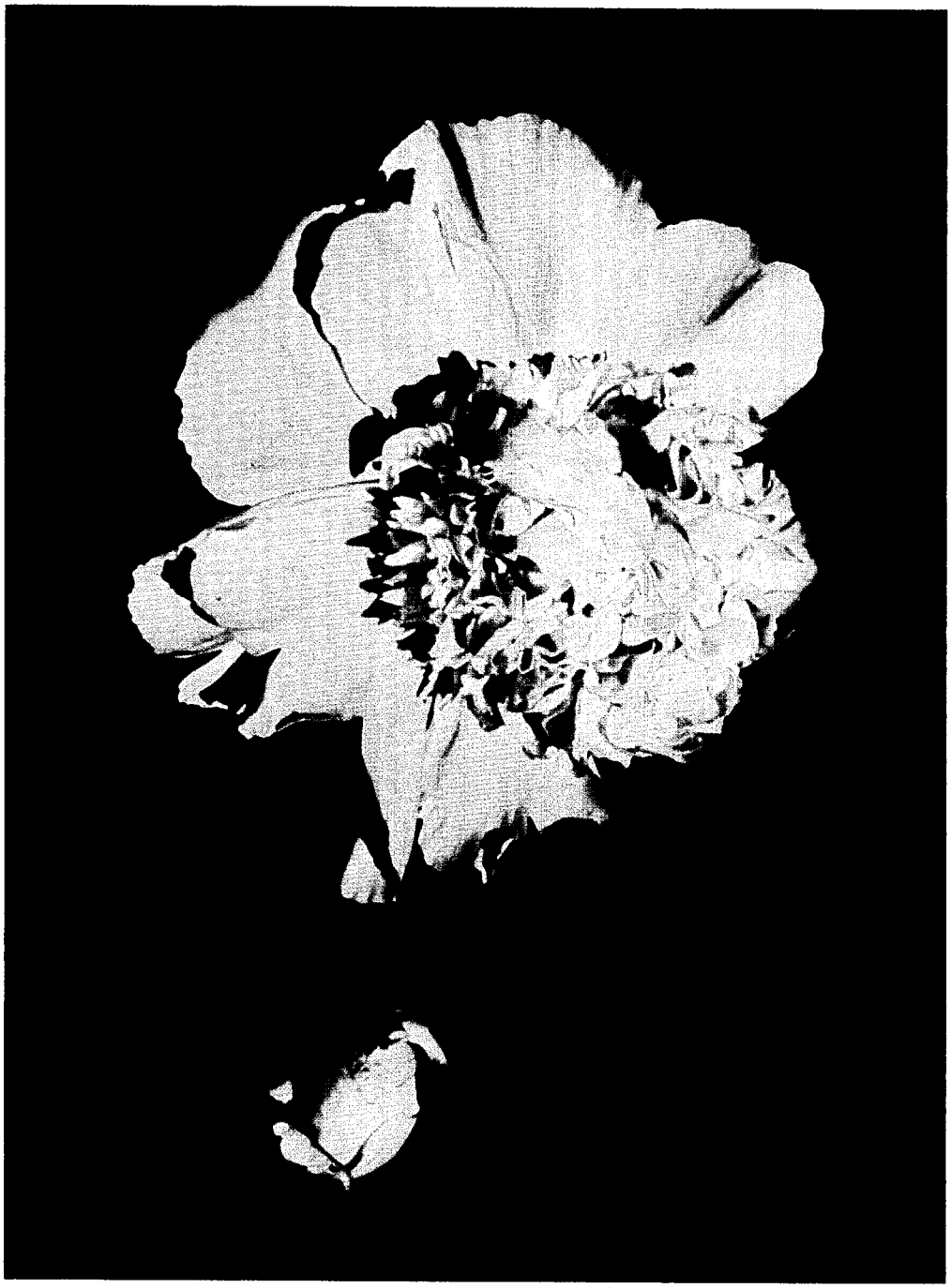

United States Patent Office

Plant Pat. 3,395
Patented Sept. 18, 1973

3,395
PEONY PLANT

Carl G. Klehm, 2 E. Algonquin Road,
Arlington Heights, Ill. 60005

Filed Mar. 9, 1972, Ser. No. 233,365
Int. Cl. A01h 5/00
U.S. Cl. Plt.—68 1 Claim The present invention relates to a new and distinct variety of peony plant, which was originated by me by crossing the peony variety known as "Mons. Jules Elie" (unpatented) with the peony variety known as "W. L. Gumm" (unpatented), the former being the seed parent and the latter being the pollen parent.

As the result of this breeding, I have produced a new and improve peony variety which is distinguished from its parents, as well as from all other peony varieties of which I am aware, as evidenced by the following unique combination of principal features which are outstanding therein:

(1) A vigorous, multi-stemmed and upright habit of growth;

(2) Very large foliage of an attractive deep green color;

(3) A free blooming habit;

(4) A neat, compact, bomb-shaped flower form, with ruffled and crinkled guard petals;

(5) A distinctive, attractive and unusual flower color, with the outer petals being pale pink, striped and splotched with darker pink hues, and with the flower center having marked tones of cream, lemon and yellow colors; and (6) An outstanding flower fragrance.

Asexual reproduction of my new peony variety by root division, as performed by me in my nurseries at Barrington and Arlington Heights, Ill., shows the foregoing characteristics and distinctions come true to form and are established and transmitted through succeeding propagations.

The accompanying drawing shows typical specimens of the vegetative growth and flowers of my new variety, as depicted in color as nearly true as it is reasonably possible to make the same in a color illustration of this character.

The following is a detailed description of my new peony variety, with color terminology in accordance with Koster's Color Guide (1931 Edition), except where color terms of ordinary dictionary significance are obvious, as based on specimens grown and observed at Barrington and Arlington Heights, Ill.:

Breeding: Seedling.
*Seed parent.*—"Mons. Jules Elie."
*Pollen parent.*—"W. L. Gumm."
Type: Hardy; outdoor; seedling.
Propagation: Holds its distinguishing characteristics through succeeding propagations by root division.

*Flower*

Blooming habit: Annual.
Blooming season: During June in Illinois.
Quantity of bloom: Free.
Continuity: One season.
Bud:
*Size.*—Large.
*Form.*—Medium length.
*Color.*—Pink (near Solferino Red, Plate 40).
*Sepals.*—Permanent; recurved; usually 3 in number. Color.—Green.
*Calyx.*—Color—Green.
*Peduncle.*—Medium length; heavy; medium smoothness. Color—Green.

Bloom:
*Borne.*—Usually singly.
*Form.*—Neat; compact; bomb-shaped.
*Petalage.*—Normal for species.
*Size.*—Open blooms average from about 8 inches to 9 inches in diameter.
*Opening.*—Opens up well from bud.
*Stems.*—Stiff; erect; heavy; from about 27 inches to 29 inches long.
*Color.*—Outer petals pale pink (nearly white), with stripes and splotches ranging from near Solferine Red, Plate 40, to near Rosy Magenta, Plate 44, with a marked glow at center of each flower combining hues of near Cream, Plate 4, near Lemon Yellow, Plate 7 and near Yellow, Plate 6.
*Discoloration.*—Some bleaching when exposed to hot sun.
*Fragrance.*—Outstanding.
Petals:
*Texture.*—Thick.
*Form.*—Notched; ruffled and crinkled guard petals.
*Lasting quality.*—Long on plant.

*Reproductive organs*

Stamens: None.
Pistils: Usually 3 in number. Color—Lemon-white.
Stigmas.—Cream-white.

*Plant*

Form: Herbaceous multi-stemmed.
Growth: Vigorous; upright.
Foliage:
*Size.*—Very large.
*Quantity.*—Normal.
*Color.*—Deep green, near Taxus Green, Plate 81.
*Shape.*—Lanceolate.
*Texture.*—Upper side—smooth. Under side—smooth.
*Margin.*—Smooth.
*Disease resistance.*—Good tolerance to ordinary diseases to which peony varieties are normally subject, as determined by comparison with other varieties grown under the same conditions at Barrington and Arlington Heights, Illinois.

*General observations*

The unusual blending of the flower colors is distinctly unique in the field of peony varieties, and combined with the distinctive and attractive flower form, makes my new variety a commercially valuable addition to the line of peony varieties heretofore available.

I claim:

1. A new and distinct variety of peony plant, substantially as herein shown and described, characterized particularly as to novelty by the unique combination of a vigorous, multi-stemmed and upright habit of growth, very large foliage of an attractive deep green color, a free blooming habit, a neat, compact, bomb-shaped flower form, with ruffled and crinkled guard petals, a distinctive, attractive and unusual flower color, with the outer petals being pale pink, striped and splotched with darker pink hues, and with the flower center having marked tones of cream, lemon and yellow colors, and an outstanding flower fragrance.

No reference cited.

ROBERT E. BAGWILL, Primary Examiner